(12) United States Patent
Thompson

(10) Patent No.: US 11,433,147 B2
(45) Date of Patent: Sep. 6, 2022

(54) FLUORESCENT FLUID FOR DETECTING FLUID INJECTION

(71) Applicant: Quaker Chemical (Australasia) Pty Ltd, Seven Hills (AU)

(72) Inventor: Wayne Thompson, Mount Victoria (AU)

(73) Assignee: Quaker Chemical (Australasia) Pty Ltd, Steven Hills (AU)

( * ) Notice: Subject to any disclaimer, the term of this patent is extended or adjusted under 35 U.S.C. 154(b) by 366 days.

(21) Appl. No.: 15/943,321

(22) Filed: Apr. 2, 2018

(65) Prior Publication Data

US 2018/0318452 A1 Nov. 8, 2018

Related U.S. Application Data

(63) Continuation of application No. 15/378,557, filed on Dec. 14, 2016, now abandoned, which is a continuation of application No. 14/199,526, filed on Mar. 6, 2014, now abandoned, which is a continuation-in-part of application No. 14/238,171, filed on Feb. 10, 2014, now abandoned.

(51) Int. Cl.
| | | |
|---|---|---|
| *A61K 49/00* | (2006.01) | |
| *C11D 3/30* | (2006.01) | |
| *G01N 33/28* | (2006.01) | |
| *C10M 171/00* | (2006.01) | |
| *C10N 40/08* | (2006.01) | |
| *C10N 40/00* | (2006.01) | |

(52) U.S. Cl.
CPC ...... *A61K 49/0017* (2013.01); *A61K 49/0021* (2013.01); *C10M 171/00* (2013.01); *C11D 3/30* (2013.01); *G01N 33/2882* (2013.01); *C10N 2040/08* (2013.01); *C10N 2040/42* (2020.05)

(58) Field of Classification Search
CPC ....... A61B 5/0071; A61B 5/06; A61B 5/4845; A61M 5/007; F02M 2200/18; F15B 20/005; F15B 21/06; G01M 3/20; G01N 21/643

See application file for complete search history.

(56) References Cited

U.S. PATENT DOCUMENTS

| | | |
|---|---|---|
| 5,421,192 A | 6/1995 | Henry |
| 6,056,162 A | 5/2000 | Leighley |

(Continued)

FOREIGN PATENT DOCUMENTS

| | | |
|---|---|---|
| CA | 879597 A | 8/1971 |
| CN | 102099671 A | 6/2011 |

(Continued)

OTHER PUBLICATIONS

Aragon et al., "Reliability of a Visual Scoring System with Fluorescent Tracers to Assess Dermal Pesticide Exposure", Ann. Occup. Hyg., vol. 48, No. 7, pp. 601-606 (2004).

(Continued)

*Primary Examiner* — Mark D Remaly
(74) *Attorney, Agent, or Firm* — Morgan, Lewis & Bockius LLP

(57) ABSTRACT

A fluorescent solution is disclosed for use in a hydraulic or diesel fluid to facilitate detection of injection of the hydraulic of diesel fluid into a human. The fluorescent solution includes a fluorescent dye and a stabilizing agent. The stabilizing agent may be a surfactant. A hydraulic fluid mixture is also disclosed which includes a fluorescent solution and a hydraulic fluid.

12 Claims, 6 Drawing Sheets

(56) References Cited

U.S. PATENT DOCUMENTS

| | | | |
|---|---|---|---|
| 6,165,384 | A | 12/2000 | Cooper et al. |
| 9,011,716 | B1 | 4/2015 | Duerr |
| 2003/0044523 | A1 | 3/2003 | Brass |
| 2005/0094147 | A1 | 5/2005 | Yaroslavsky et al. |
| 2011/0117025 | A1 | 5/2011 | Dacosta et al. |
| 2013/0062563 | A1 | 3/2013 | Zhou et al. |

FOREIGN PATENT DOCUMENTS

| | | |
|---|---|---|
| EP | 2098156 A1 | 9/2009 |
| JP | H08128916 A | 5/1996 |
| JP | H1130594 A | 2/1999 |
| RU | 2007104289 A | 5/2007 |
| RU | 2014105444 A | 10/2015 |
| WO | 92/07249 | 4/1992 |
| WO | 2005/027730 A2 | 3/2005 |
| WO | 2005/052560 A1 | 6/2005 |
| WO | 2009140757 | 11/2009 |
| WO | 2009140757 A1 | 11/2009 |
| WO | 2013029082 A1 | 3/2013 |

OTHER PUBLICATIONS

Aragon et al., "Assessment of Dermal Pesticide Exposure with Fluorescent Tracer: A Modification of a Visual Scoring System for Developing Countries", Ann. Occup. Hyg., vol. 50, No. 1, pp. 75-83 (2006).

Cherrie et al., "Use of Qualitative and Quantitative Fluorescence Techniques to Assess Dermal Exposure", Ann. Occup. Hyg., vol. 44, No. 7, pp. 519-522 (2000).

Crismon et al., "Studies of Gangrene Following Cold Injury. V. The Use of Fluorescein as an Indicator of Local Blood Flow: Fluorescein Tests in Experimental Frostbite", Sep. 1, 1946, pp. 268-276.

Davis, Pinpointing Vehicle Leaks Fasterwith Ultraviolet Light, Materials Evaluation, vol. 47, pp. 1248-1250 (1989).

Doyle, "A System for the Management of Ricks from Pressurised Fluids", NSW Minerals Council—Occupational Health & Safety Conference, Jul. 2011.

Fenske, "Visual Scoring System for Fluorescent Tracer Evaluation of Dermal Exposure to Pesticides", Bull. Environ. Contam. Toxicol., vol. 41, pp. 727-736 (1988).

Fenske, "Dermal Exposure Assessment Techniques", Ann. Occup. Hyg., vol. 37, No. 6, pp. 687-706 (1993).

Fenske, "Nonuniform Dermal Deposition Patterns during Occupational Exposure to Pesticides", Arch. Environ. Contam. Toxicol., vol. 19, pp. 332-337 (1990).

Jonak et al., "Intradermal Indocyanine Green for In Vivo Fluorescence Laser Scanning Microscopy of Human Skin: A Pilot Study", PLoS ONE, vol. 6, No. 8, e23972 (2011).

Karlbauer et al., "High-Pressure Injection Injury: A Hand-Threatening Emergency", The Journal of Emergency Medicine, vol. 5, pp. 375-379 (1987).

Marrano, "Fluorescent Tracer Additives as a Nondestructive Inspection Technique for Leak Testing", Materials Evaluation, pp. 436-438 (1993).

Semple, "Dermal Exposure to Chemicals in the Workplace: Just How Important is Skin Absorption?", Occup Environ Med, vol. 61, pp. 376-382 (2004).

Spectroline Corporation, "Fluorescent Leak Detection for Industrial Systems", May 20, 2010 http://web.archive.org/web/20100529021051/http://www.spectroline.com/industrial/industrialproducts.html.

Swindle et al., "View of Normal Human Skin In Vivo as Observed Using Fluorescent Fiber-Optic Confocal Microscopic Imaging", The Journal of Investigative Dermatology, vol. 121, No. 4, pp. 706-712 (2003).

Vo-Dinh et al., "The lightpipe luminoscope for monitoring occupational skin contamination", Am. Ind. Hyg. Assoc. J., vol. 42, pp. 112-120 (1981).

European Search Report for Application EP 12 82 7019 dated Mar. 20, 2015.

Magnusson et al., "Broad and complex antifungal activity among environmental isolates of lactic acid bacteria", FEMS Microbiology Letters, vol. 219, pp. 129-135 (2003).

Schnuerer et al., "Antifungal lactic acid bacteria as biopreservatives", Trends in Food Science & Technology, vol. 16, pp. 70-78 (2005) Abstract Only.

Verhoeven et al., "High-Pressure Injection Injury of the Hand: An Often Underestimated Trauma: Case Report with Study of Literature", Strat Traum Limb Recon, vol. 3, pp. 27-33 (2008).

Vasilevski et al., "High-Pressure Injection Injuries to the Hand", Am J Emerg Med, vol. 18, pp. 820-824 (2000).

Rohm and Haas, "Flourescent Yellow 131 SC Product Descriptor," Oct. 2006, pp. 3.

Commonwealth of Australia, "Statutory Declaration made by Glen Lilly," dated May 20, 2014.

International Search Report for PCT/AU2012/000094 dated Mar. 26, 2012.

U.S. Appl. No. 16/111,738, Office Action dated Jun. 14, 2019.

Canadian Patent Application No. 2883777 Search Report dated Dec. 13, 2018.

Dailiana et al., Injection injuries: seemingly minor injuries with major consequences, 2008, vol. 12, pp. 33-36.

European Search Report for EP 20155942; dated Jul. 15, 2020; 2 pages.

European Search Opinion for EP 20155942; dated Jul. 15, 2020; 8 pages.

Brazilian Preliminary Examination for BR 112014004260-8; dated Feb. 2, 2020; 4 pages.

English translation of Brazilian Preliminary Examination for BR 112014004260-8; dated Jun. 1, 2020; 5 pages.

Canadian Office Action for CA 2,883,777; dated Dec. 13, 2018; 4 pages.

Dailiana et al., "Injection injuries: seemingly minor injuries with major consequences", Hippokratia, 12(1): 33-36, 2008.

"Fluid Dye Identifies Hydraulic System Leaks," http://hydraulicspneumatics.com/200fTechZone/HydraulicFluids/Aricle/False/87722/TechZone-HydraulicFluids, Aug. 2011.

Office Action for corresponding Canadian Patent Application No. 2,883,777 dated Mar. 8, 2018, 4 pages.

English Translation of Office Action for corresponding Russian Patent Application No. 2017145799 dated Mar. 29, 2021, 7 pages.

English Translation of Search Report for corresponding Russian Patent Application No. 2017145799 dated Mar. 25, 2021, 2 pages.

Office Action for Russian Application No. 2017145799 dated Aug. 2, 2021, 4 pages.

Technical Opinion for Brazilian Application No. 112014004260-8 dated Aug. 4, 2021, 4 pages.

Dan et al., "1% Lymphazurin vs 10% Fluorescein for Sentinel Node Mapping in Colorectal Tumors," Arch. Surg., 2004, 130:1180-1184.

Translation of Office Action for Russian Application No. 2017145799 dated Aug. 2, 2021, 4 pages.

Jonak, C. et al., "Intradermal Indocyanine Green for In Vivo Fluorescence Laser Scanning Microscopy of Human Skin: A Pilot Study," PLoS One, 2011, 6(8):e23972.

Office Action for Russian Application No. 2017145799 dated Nov. 26, 2021, 14 pages.

Denial for Brazilian Application No. 112014004260-8 dated Nov. 25, 2021, 5 pages.

FLUORESCENT FLUID FOR DETECTING FLUID INJECTION

CROSS-REFERENCE TO RELATED APPLICATIONS

The present invention is a continuation of U.S. patent application Ser. No. 15/378,557, filed on Dec. 14, 2016, which is a continuation of U.S. patent application Ser. No. 14/199,526, filed on Mar. 6, 2014, which is a continuation-in-part of U.S. patent application Ser. No. 14/238,171, filed on Feb. 10, 2014, all of the disclosures of which are incorporated herein by reference in their entireties.

FIELD OF THE INVENTION

The present invention relates to the detection of an outside fluid injected into the human body and, in particular, to a fluorescent fluid for use in the detection of hydraulic and fuel fluid within the human body. The invention has been primarily developed for use in detecting the presence of hydraulic and diesel fuel in the human body as a result accidental fluid injection and will be described hereinafter with reference to this particular use. However, it will be appreciated that the invention is not limited to this particular field of use.

BACKGROUND OF THE INVENTION

In this specification unless the contrary is expressly stated, where a document, act or item of knowledge is referred to or discussed, this reference or discussion is not an admission that the document, act or item of knowledge or any combination thereof was at the priority date, publicly available, known to the public, part of common general knowledge; or known to be relevant to an attempt to solve any problem with which this specification is concerned.

Hydraulic and diesel fuel systems machinery such as those in mining and other industrial applications, operate at very high pressures, often 207 bar (3000 psi) and above. Loose connections or defective or failures in hoses can cause a fine, high velocity stream of fluid to be ejected which can be hazardous to a human that comes into contact with the stream. Testing has shown that even in systems pressurised to as little as 7 bar (100 psi), this fluid stream can penetrate human skin.

An injury sustained in a high pressure injection incident is, in many cases significantly worse than it will first appear since hydraulic or diesel fuel inside the body can cause tissue damage. Such since injuries is relatively rare, medical practitioners or hospital services may not be alert to the severity of an injury of this type.

An accidental fluid injection beneath the skin may initially only produce a slight stinging sensation. The danger is that a victim will tend to ignore this, thinking that it will get better with time. This is not often the case and the fluid can cause serious tissue damage. Fluid injected directly into a blood vessel can spread rapidly through a victim's circulatory system leaving the human body with little ability to purge these types of fluid.

A fluid injection injury can become very serious or even fatal if not dealt with promptly and properly. Typically the only treatment available is to surgically remove the fluid within a few hours of injection. The longer the delay in getting professional medical aid, the further the tissue damage can spread. If left untreated, the injury could result in disfigurement, amputation of the affected part or death of the victim.

Accidental fluid injections can be difficult to confirm. In many cases the victim may be covered by fluid externally, resulting in uncertainty on whether any fluid has penetrated the victim's skin. As discussed above any delay in treating a victim can cause severe harm and, as such, it would be advantageous if confirmation of fluid injection can be confirmed.

SUMMARY OF THE INVENTION

It is an object of the present invention to overcome or ameliorate at least one of the disadvantages of the prior art, or to provide a useful alternative.

According to a first aspect of the invention there is provided a fluorescent solution for use in a detection system that helps locate a fluid injected beneath a patient's skin. The fluorescent solution includes a fluorescent dye and a stabilizing agent. In one embodiment, the stabilizing agent is a surfactant compound. The surfactant is preferably monoethanolamine.

In one embodiment of the invention the fluorescent solution comprises about 0.1% stabilizer and about 99.9% fluorescent dye. In another embodiment of the invention the fluorescent solution comprises about 2% stabilizer and about 98% fluorescent dye.

The present invention is also directed to a hydraulic fluid mixture comprising a fluorescent solution which includes a fluorescent dye and a hydraulic fluid. The fluorescent solution preferably comprises about 0.12% of the mixture, and the hydraulic fluid comprises about 99.88% hydraulic oil. In another embodiment, the fluorescent solution comprises about 0.015% of the mixture, and the remainder is a hydraulic fluid.

The foregoing and other features of the invention and advantages of the present invention will become more apparent in light of the following detailed description of the preferred embodiments, as illustrated in the accompanying figures. As will be realized, the invention is capable of modifications in various respects, all without departing from the invention. Accordingly, the drawings and the description are to be regarded as illustrative in nature, and not as restrictive.

BRIEF DESCRIPTION OF THE DRAWINGS

A preferred embodiment of the invention will now be described, by way of example only, with reference to the accompanying drawings in which.

PREFERRED EMBODIMENTS OF THE INVENTION

Figure 1:
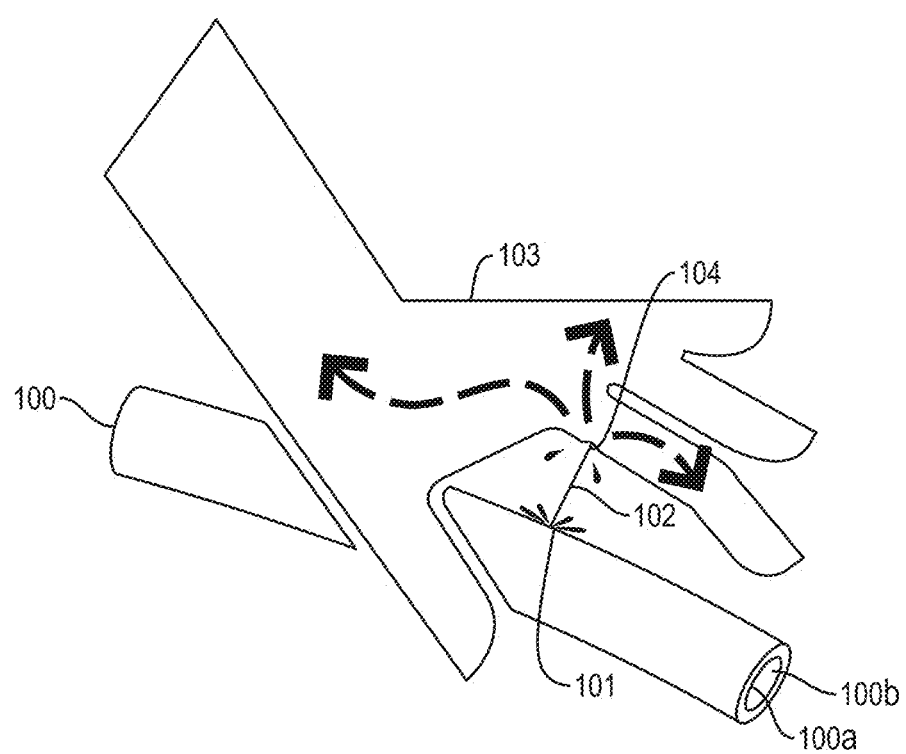
FIG. 1 is a view of a fluid injection according to the invention.

The preferred embodiment of the invention provides a fluorescent fluid for use in a system or method for detecting fluid injection in a patient following a possible fluid injection. The method includes the step of providing a fluid storage tank in the form of equipment having a diesel or hydraulic tank. An appropriate fluid, such as diesel or hydraulic fluid, is added to the fluid storage tank. A fluorescent dye according to the present invention is then provided and added to the fluid such that the fluid is capable of fluorescing in the presence of ultraviolet, violet or blue light. It would be understood that the fluorescent dye can be added to any suitable fluid and the scope of the invention is not limited to diesel and hydraulic fluid. In one embodiment, the fluid dye includes a stabilizing agent configured to delay or reduce the dispersing or quenching of the dye within the human body as will be discussed in more detail below. Quenching refers to the breakdown of the fluorescent capabilities of a dye that can occur when the chemical structure is disrupted, thereby preventing the dye from entering into an excited state from which it can fluoresce. As used herein, the combination of the fluorescent dye and the stabilizing agent is referred to herein as the fluorescent solution.

The preferred embodiment of the invention also provides a fluid reservoir, the fluid reservoir adapted to store hydraulic fluid and fluorescent solution such that the hydraulic fluid and the fluorescent solution mix in the fluid reservoir. The fluid reservoir is connected to and is in fluid communication with at least one hydraulic actuator and/or motor in a hydraulic tool or that is part of a hydraulic machine or system, such that the flow of hydraulic fluid and the fluorescent solution is utilized by the actuator and/or motor during operation of the tool, or machine/system. As would be understood, the hydraulic system can be used to drive any number of motors, pumps and the like and many different types of machinery used in mining and in other applications. The fluid reservoir is connected to the at least one hydraulic actuator and/or motor by any conventional components, includes a hydraulic tube; a hydraulic pipe; a hydraulic hose or the like. The combination of the hydraulic fluid and fluorescent solution is such that a leak in any component in the hydraulic system through which the mixture flows, including the hydraulic tube, hydraulic pipe or hydraulic hose, will result in the mixed hydraulic fluid and fluorescent solution leaking out.

As would be understood, a broad spectrum of light could be used in embodiments of the invention and the invention is not limited to light of any particular wavelength or color. However, a preferred light is one that emits light in long wave ultraviolet (UV-A) wavelength range of about 320 nm to about 400 nm, in the medium wave ultraviolet (UV-B) range from about 280 nm to about 320 nm, in the short wave ultraviolet (UV-C) range, for example, around 254 nm, or in the visible violet/blue range from about 400 nm to about 500 nm within the electromagnetic spectrum.

In one preferred embodiment, the fluorescent dye used is sold by Spectronics Corporation under the brand names Oil-Glo® or Water-Glo® fluorescent dye. Oil-Glo® fluorescent dye is a combination of an oil and a naphthalimide fluorescent dye concentrate. Water-Glo® fluorescent dye is a combination of deionized water and a fluorescent dye concentrate. As would be understood any other suitable fluorescent dye can be used and chosen according to the particular application and specifications required.

As discussed above, the fluorescent dye will generally begin to disperse in the human body shortly after injection, or its fluorescent capabilities would be quenched. As a result, any delay in locating the injected fluid could make subsequent detection difficult. For example, in one test the fluorescent dye began to disperse or quench in as little as 25 minutes. One way to delay the dispersing/quenching of the fluorescent dye is to add a stabilizer that acts with the fluorescent dye to extend the dye's ability to be detected through its fluorescence. One suitable stabilizer that testing has shown extends the detectability of the fluorescent dye is a surfactant compound, such as a monoethanolamine (MEA). Other hydrophobic/hydrophilic compounds and surfactants are capable of acting as stabilizer for the fluorescent dyes. For example, the Solcenic 2020 hydraulic fluid emulsifying agent sold by Fuchs Lubricants Pty Ltd., is a petroleum oil mixture which contains various constituent compounds that act as a stabilizer when used with a fluorescent dye. Other useful stabilizers include, for example, emulsifying agents used in hydraulic fluids used for longwall mining equipment such as Solcenic HL available from Fuchs Lubricants Pty Ltd., Quintolubric® 814 and Quitolubric® 818 fluids, both available from Quaker Chemical Corporation. Other forms of chemicals that are alternatives to monoethanolamine and would be useful as stabilizers are [the terms listed in brackets are CAS reference numbers]: C10-C16 ethoxylated alcohol [68002-97-1]; C12-15 alcohol, ethoxylated [68131-39-5]; ethoxylated 4-tert-octylphenol [9002-93-1]; ethoxylated alcohol [68439-50-9, 126950-60-5, and 66455-15-0]; ethoxylated alcohol (C10-12) [67254-71-1]; ethoxylated alcohol (C14-15) [68951-67-7]; ethoxylated alcohol (C9-11) [68439-46-3]; ethoxylated alcohols (C12-14 secondary) [84133-50-6]; ethoxylated alcohols (C12-14) [68439-51-0]; ethoxylated branch alcohol (78330-21-91; ethoxylated C11 alcohol [34398-01-1]; ethoxylated castor oil [61791-12-6]; ethoxylated fatty acid, coco [61791-29-5]; ethoxylated fatty acid, coco, reaction product with ethanolamine [61791-08-0]; ethoxylated hexanol [68439-45-2]; ethoxylated octylphenol [9036-19-5]; ethoxylated sorbitan monostearate [9005-67-8]; ethoxylated sorbitan trioleate [9004-70-3]; fatty acids [61790-12-3]; fatty acids, tall oil reaction products with acetophenone, formaldehyde & thiourea [6818 8-40-9]; fatty alcohol polyglycol ether surfactant [9043-30-5]; polyoxylated fatty amine salt [61791-26-2]; tall oil fatty acid diethanolamine [68155-20-4]; tallow fatty acids sodium salt [8052-48-0]; 4-nonylphenol polyethylene glycol ether branched/nonylphenol ethoxylated/oxyalkylated phenol [127087-87-0]; alcohols, C12-C16, ethoxylated (a.k.a. ethoxylated alcohol) [68551-12-2]; alkylphenol ethoxylate surfactants [9016-45-9]; amines, C12-14-tert-alkyl, ethoxylated [73138-27-9]; amines, ditallow alkyl, ethoxylated [71011-04-6]; and amines, tallow alkyl, ethoxylated, acetates [68551-33-7]. the following should also provide some degree of stabilization: 2-propenoic acid, homopolymer, ammonium salt [9003-03-6]; cellulase/hemicellulase enzyme [9012-54-8]; cellulose [9004-34-6]; cocamidopropyl betaine [61789-40-0]; dodecylbenzene [123-01-3]; formaldehyde [50-00-0]; formamide [75-12-7]; formic acid [64-18-6]; fumaric acid [110-17-8]; glycerol/glycerine[56-81-5]; guar gum [9000-30-0]; hemicellulase [9025-56-3]; hydroxyethyl cellulose [9004-62-0]; isoparaffinic petroleum hydrocarbons, synthetic [64742-88-7]; light paraffin oil [1120-21-4]; naphthalene [91-20-3]; potassium acetate [127-08-2]; sodium polyacrylate [9003-04-7]; carboxymethylhydroxypropyl guar

[68130-15-4]; hydroxypropyl guar [39421-75-5]; vinylidene chloride/methylacrylate copolymer [25038-72-6]; 2-propen-1-aminium, n,n-dimethyl-n-2-propenyl-chloride, homopolymer [26062-79-3]; and polyoxyethylene sorbitan monooleate [9005-65-6].

The combination of the fluorescent dye and the stabilizer forms a fluorescent solution which can then be added to a suitable hydraulic fluid. In one embodiment, an oil-based fluorescent solution is made comprising about 0.1% Solcenic 2020 fluid and about 99.9% Oil-Glo® fluorescent dye. In another embodiment, a water-based fluorescent solution is made comprising about 2% Solcenic 2020 fluid and about 98% Water-Glo® fluorescent dye. Of course, as with the Solcenic fluid, the stabilizer may already be included in an oil and, thus, the fluorescent dye could be added directly to the oil.

In use, the fluorescent solution is then added to the working fluid, such as a hydraulic fluid used in machinery. One dilution that has been found to provide sufficient fluorescent response upon leakage is about 0.12% of the oil-based fluorescent solution is added to about 99.88% hydraulic oil. In another working dilution, about 0.015% of the water-based fluorescent solution was added to about 99.985% of Solcenic 2020 (which consists of about 2%-4% Solcenic concentrate and the remainder water).

Following a suspected fluid injection, the present invention provides a method for detecting whether there has been a fluid injection into an individual. The method includes the steps of providing a lamp configured to emit light which causes the fluorescent dye to fluoresce. In the preferred embodiment the light is a high intensity blue light although, as discussed above, it would be understood that any suitable light emitting a wavelength between about 254 nm and 500 nm could be used. Since the high pressure stream of fluid from the hydraulic machinery would contain a combination of hydraulic fluid mixed with the fluorescent solution, if the person has been injected by the stream, the hydraulic fluid and fluorescent solution mixture would be injected into the person. Using the fluorescent illumination lamp, the injection point along with the injected tissue can be found as the fluid mixture in the tissue will fluoresce as the light is passed over the skin.

In order to facilitate detection, once a suspected fluid injection occurs, the it is preferable that an individual is brought to a dark room or location and examined with the blue light to determine whether possible fluid injection has occurred. The possibility of fluid injection would be if there is fluorescence on the skin of the individual, such as at or near locations of bleeding. After the initial examination, if there is the possibility of fluid injection, the method next involves the step of washing the patient, and particularly the point of possible fluid injection, preferably with water and detergent to clean off any hydraulic fluid or other contaminants on the surface of the skin that might give a false reading or obscure detection.

After the step of washing the patient and the point of possible fluid injection, the method includes the step of re-examining the patient with the blue light in the dark room to confirm whether possible fluid injection has occurred.

By following the steps of the preferred embodiment, it is possible to determine whether or not fluid injection has occurred in the patient.

FIG. 1 shows a view of a fluid injection according to the invention. Tubing 100 has pressurised fluid such as hydraulic fluid 100a flowing through it. The hydraulic fluid 100a has a fluorescent solution 100b added to it. Tubing 100 includes a leak 101 that has resulted in a high pressure stream 102. In this instance a patient's hand 103 is in the way of the stream and the hand 103 receives a fluid injection through injection point 104.

Following the fluid injection the following steps are followed:

1. Confirm the fluid has been mixed with the recommended fluorescent solution, such as Oil-Glo® fluorescent dye and a stabilizing agent in accordance with the applicable design application schedule. Specifically does the fluid that's escaped under pressure visibly glow when illuminated with a blue or UV light source.
2. If suspected fluid inject ion occurs immediately follow any fluid injection protocol and utilise the high intensity blue light on the surface of the area.
3. Confirm that paramedics or other medical staff on site or in attendance are conversant with the use of the blue light and the detection system of the present invention.
4. Ensure that the person that has potentially received a fluid injection is taken to a dark environment and scanned with the approved blue light prior to washing the affected area.
5. Wash the affected area utilising copious amounts of water and any industrial hand and face soap or detergent.
6. Ensure that the person that has potentially received a fluid injection is taken to a dark environment and rescanned with the approved blue light.
7. If fluorescence is detected on the surface of the skin then the patient should be taken for immediate medical care to have the fluid removed through surgery or other suitable manners.

The following examples show test results of fluid escaping under pressure at a distance of 0 mm ↔100 mm, an escape pressure of 10 bar increasing to 207 Bar and a flow rate of 2.2 lpm. The fluid used in the test is Solcenic 2020 fluid with a ratio of 98% water, 2% Solcenic concentrate combined with Oil-Glo® fluorescent dye.

Figure 2:
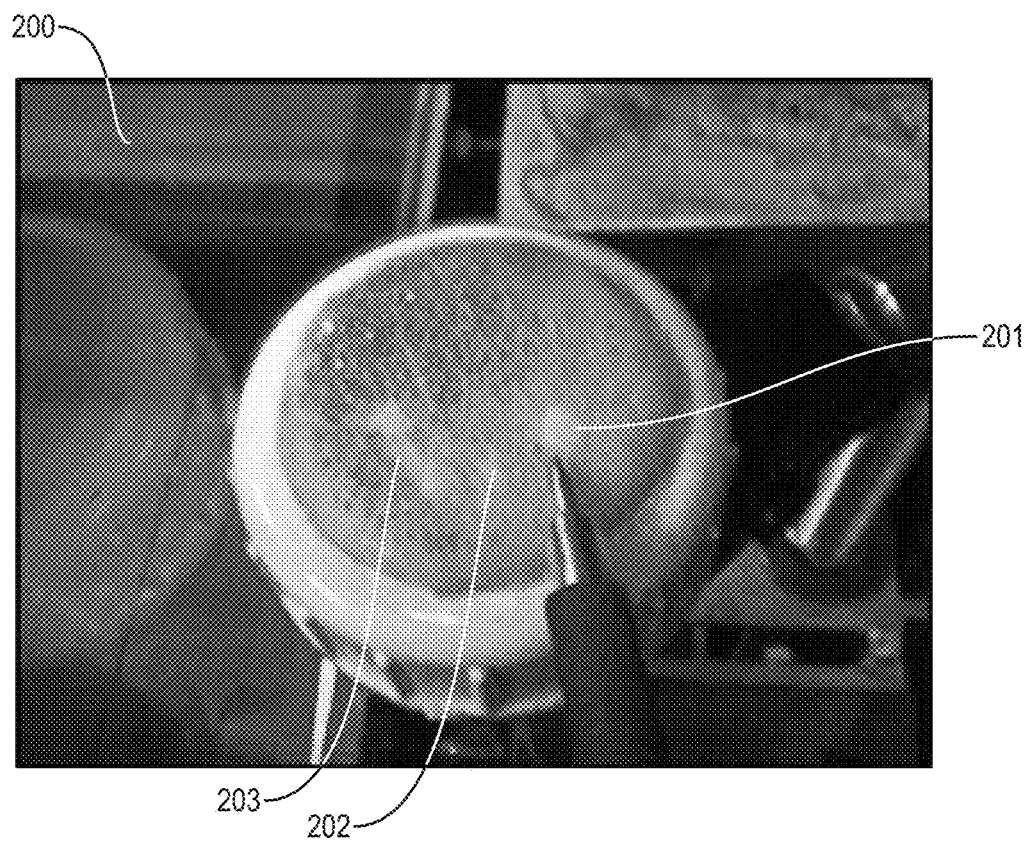
FIG. 2 a picture of a fluid injection according to the invention.

Referring to FIG. 2 there is shown a tissue sample 200 under blue light that has received a fluid injection. In this example, evidence visible after affected area has been washed indicates a fluid injection has occurred. In this example the penetration of human skin occurs at 172 Bar (2500 psi) @ 100 mm @ 2.2 lpm.

Figure 3:
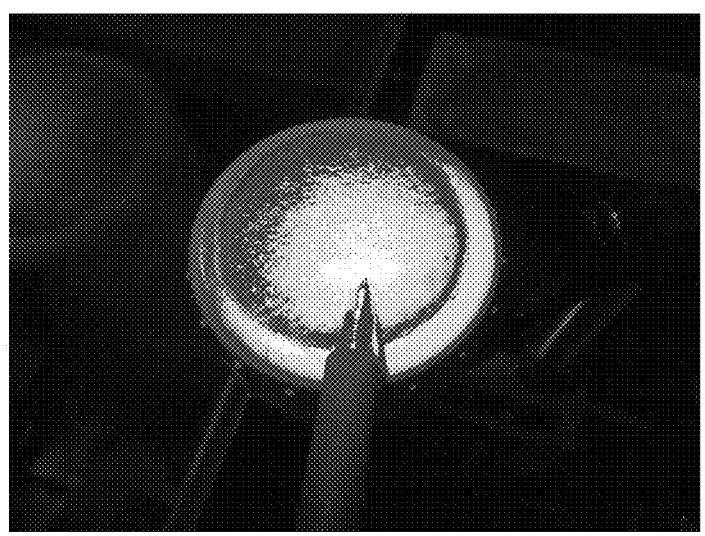
FIG. 3 shows a tissue sample according to the invention.

FIG. 3 shows penetration of human skin at 138 Bar (2000 psi) @ 100 mm @2.2 lpm

Figure 4:
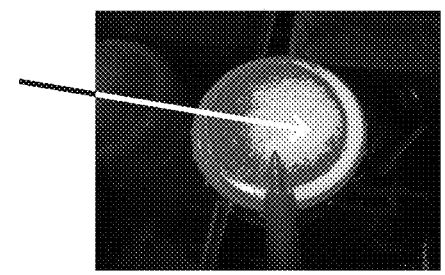
FIG. 4 shows a tissue sample according to the invention.

FIG. 4 shows penetration of human skin −103 Bar (1500 psi) @ 100 mm @2.2 lpm. This photo represents the surface of the tissue and clearly highlights an injection from the underside of the tissue.

Figure 5:
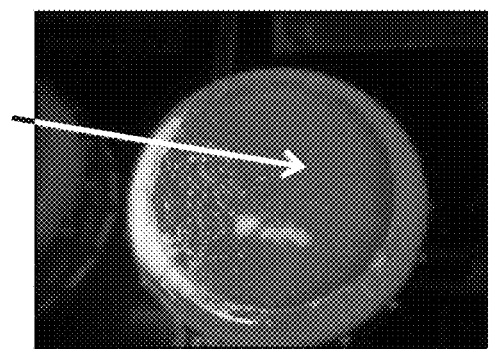
FIG. 5 shows a tissue sample according to the invention.

FIG. 5 shows penetration of human skin −34 Bar (500 psi) @ 100 mm @ 2.2 lpm. This photo represents the surface tissue and clearly highlights an injection under the surface of the tissue.

Figure 6A:
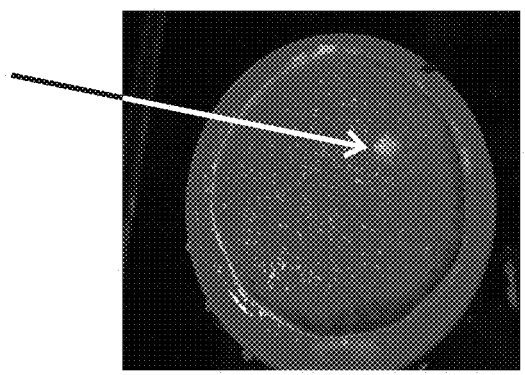
FIGS. 6a and 6b shows a tissue sample according to the invention.
Figure 6B:
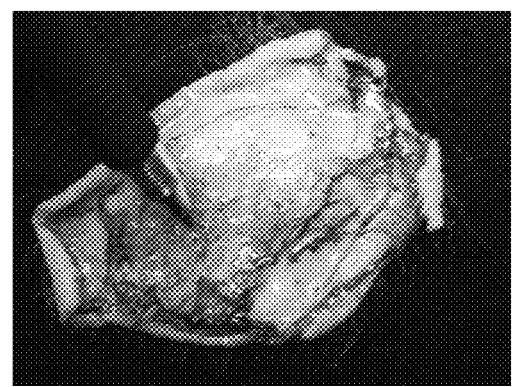

FIG. 6 shows penetration of human skin −10 Bar (145 psi)@ 100 mm @ 2.2 lpm. FIG. 6a shows the surface of the tissue and is clearly visible under UV light and associated Oil-Glo® fluorescent dye. FIG. 6b represents the underside of the tissue and is visible under UV light and associated Oil-Glo® fluorescent dye.

Figure 7A:
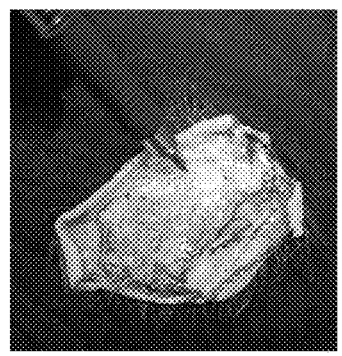
FIGS. 7a and 7b shows a tissue sample according to the invention.
Figure 7B:
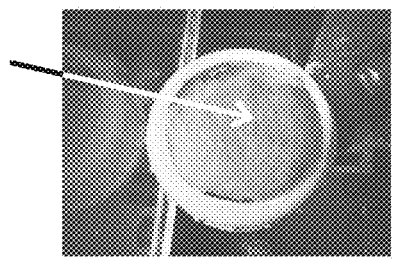

FIG. 7 shows penetration of human skin −10 Bar (145 psi) @ 50 mm @ 2.2 lpm. FIG. 7a represents the underside of the tissue and clearly highlights that fluid will break the skin. FIG. 7b represents the surface of the tissue and is visible under UV light and associated Oil-Glo® fluorescent dye.

In relation to the samples shown above, the oil was injected under pressure from the underside of each sample.

Figure 8A:
FIGS. 8a and 8b shows a fluid according to the invention.
Figure 8B:
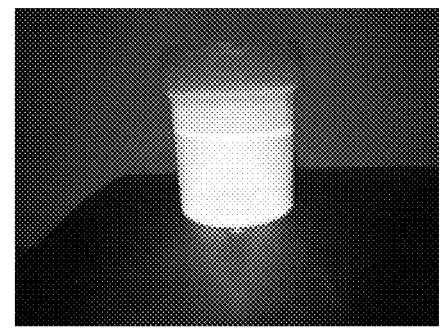

FIG. 8a shows a sample of standard hydraulic oil (ISO 68) photographed under high intensity blue light. FIG. 8b shows the sample of standard hydraulic oil (ISO 68) with 0.20% Oil-Glo® fluorescent dye additive photographed under high intensity blue light.

Figure 9A:
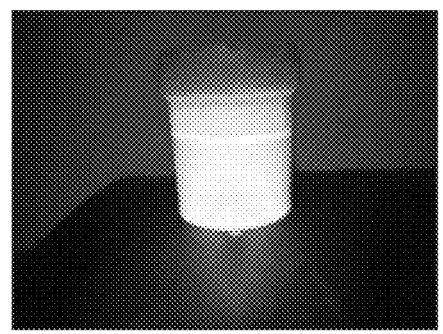
FIGS. 9a and 9b shows a fluid according to the invention.
Figure 9B:
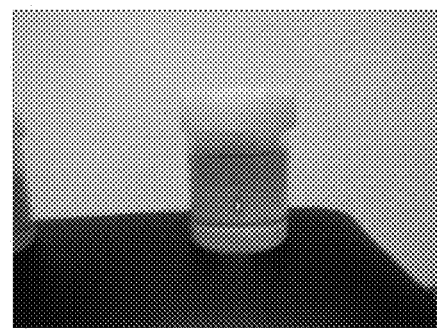

FIG. 9a shows a sample of 100% Solcenic 2020 photographed under high intensity blue light. FIG. 9b shows the sample of 100% Solcenic 2020 with the Oil-Glo® fluorescent dye additive @ 0.01% and photographed under high intensity blue light.

The preferred embodiment of the invention advantageously allows reliable detection in deep tissues which allows triage of cases not requiring surgery and also guides any surgery required, thus, potentially limiting the soft tissue surgical dissection required.

Embodiments of the invention extend to kits supplied with lights to detect the presence of the fluorescent dye in a patient.

Figure 10:
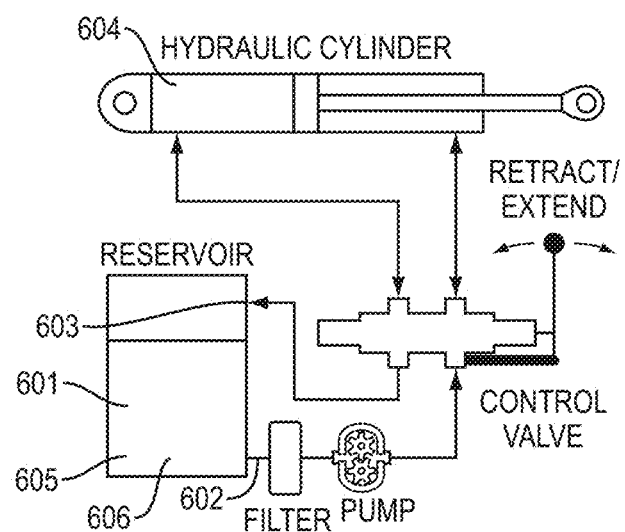
FIG. 10 shows a hydraulic system according to the invention.

FIG. 10 shows a typical hydraulic system with a reservoir tank 601, outlet 602 and inlet 603. Hydraulic fluid 606 is pumped out of the outlet 602 and through the hydraulic circuit which drives hydraulic cylinder 604. According to preferred embodiments, fluorescent solution 605 is added to the hydraulic fluid 606 preferably by adding it into the reservoir tank 601 in a dilution amount appropriate for the intended hydraulic fluid 606 based on the type and amount of fluid in the system. The hydraulic fluid 606 and the dye 605 then mix and both the fluid and the dye are pumped around the hydraulic circuit. Accordingly if there is a leak at any point in the system the mixture of both hydraulic fluid and dye is expelled through any leaks. This allows leaks to be detected and allows fluid injection in any patients to be detected in accordance with the disclosure above.

Further embodiments of the invention extend to systems and method for detecting leaks in hydraulic or fuel systems. In a similar manner as described above, a suitable dye (not necessarily fluorescent) can be added to the hydraulic tank of machinery such that the dye colors the hydraulic liquid causing it to take on the colour characteristics of the dye. The dye need not in these embodiments be fluorescent but could be chosen according to color characteristics that could be easily seen in the specific environment in which the machinery operates. In addition, embodiments of the invention include any number of liquids to which the dye could be added. For example diesel, petrol, oil, water are just some of the liquids to which a suitable dye could be added according to embodiments of the invention.

Advantages of the invention include the following:
Long term injuries are significantly reduced as the present invention may be used as the first protocol on site for identification of any suspected fluid injection injury prior to any additional medical treatment;
Environmentally safe;
Soluble with all mineral oils, emulsions, gear oils, water and engine oil (MSDS included);
Increases machine availability (highlights oil leaks);
Endorsed by major OEM'S and currently used for life of machine in all hydraulic systems;
Highly visible on the surface of the human skin;
Highly visible in soft tissue underneath the human skin;
Approved UV/Blue light can also be used for leak detection and NDT in many other engineering applications; and
Reduces surgery and rehabilitation as this product is highly visible on an under the skin as described above.

Although the invention has been described with reference to specific examples, it will be appreciated by those skilled in the art that the invention may be embodied in many other forms.

The invention claimed is:

1. A method for detecting an accidental industrial fluid injection in a patient of an industrial fluid by machinery that operates under high pressure, the method comprising the steps of:
providing the industrial fluid for use in the machinery, wherein the industrial fluid includes a fluorescent dye,
providing a lamp emitting light of a wavelength between about 254 nm and about 500 nm, wherein the light causes the industrial fluid with the fluorescent dye to fluoresce,
examining the patient with the light in a dark environment following a possible accidental fluid injection; and
detecting a presence of fluorescence in the patient wherein the light causes the fluorescent dye to fluoresce, wherein the presence of the fluorescence in the patient indicates a possible accidental industrial fluid injection.

2. The method of claim 1, wherein the light of a wavelength between about 254 nm and 500 nm is a blue light, a violet light, or an ultraviolet light.

3. The method of claim 1, wherein the step of examining the patient with the light in the dark environment further comprises the step of washing a potentially fluid-injected affected area of the patient.

4. The method of claim 3, wherein the patient is examined with the light before washing, after washing, or both before and after washing.

5. The method of claim 1, wherein the step of examining the patient with the light in the dark environment further comprises identifying a point where the accidental industrial fluid injection occurred in the patient.

6. The method of claim 5, wherein the patient is washed at a point of possible accidental industrial fluid injection in the patient.

7. The method of claim 6, wherein the step of examining the patient with the light in the dark environment further comprises inspecting, with the light, an area of skin around a point of accidental industrial fluid injection in the patient before washing, after washing, or both before and after washing.

8. The method of claim 1, further comprising determining that the accidental industrial fluid injection has occurred in the patient by detecting fluorescence of the fluorescent dye of the industrial fluid under skin of the patient.

9. The method of claim 1, wherein the accidental industrial fluid injection occurred in the patient upon a pressurized release of the industrial fluid from the machinery.

10. The method of claim 1, wherein the industrial fluid for use in machinery is hydraulic fluid or fuel.

11. The method of claim 1, wherein the machinery is hydraulic machinery having a fluid storage tank, wherein the fluid storage tank is connected to, and in fluid communication with a hydraulic actuator, a hydraulic motor, or both, and wherein the fluid communication is through a hydraulic tube, a hydraulic pipe, or a hydraulic hose.

12. The method of claim 11, wherein the industrial fluid is hydraulic fluid, and wherein flow of hydraulic fluid drives the hydraulic actuator, the hydraulic motor, or both.

* * * * *